United States Patent
Ward et al.

(10) Patent No.: US 8,851,588 B2
(45) Date of Patent: Oct. 7, 2014

(54) SLIDING DRAWER STORAGE RACK FOR COLD STORAGE UNITS

(75) Inventors: Dennis D. Ward, Vincent, OH (US); John P. Hutchinson, Marietta, OH (US); Steven A. George, Vienna, WV (US)

(73) Assignee: Thermo Fisher Scientific (Asheville) LLC, Asheville, NC (US)

(*) Notice: Subject to any disclaimer, the term of this patent is extended or adjusted under 35 U.S.C. 154(b) by 19 days.

(21) Appl. No.: 13/488,622

(22) Filed: Jun. 5, 2012

(65) Prior Publication Data

US 2013/0320833 A1 Dec. 5, 2013

(51) Int. Cl.
A47B 88/00 (2006.01)
A47B 96/04 (2006.01)

(52) U.S. Cl.
USPC ........................................ 312/348.3; 312/408

(58) Field of Classification Search
CPC ........................................................ A47B 88/20
USPC .................. 312/402, 404, 408, 348.3, 330.1; 108/60, 61, 143; 248/298.1
See application file for complete search history.

(56) References Cited

U.S. PATENT DOCUMENTS

| | | | | |
|---|---|---|---|---|
| 751,466 A * | 2/1904 | Colling | ........................... | 211/162 |
| 1,545,016 A * | 7/1925 | Sessions | ........................... | 384/23 |
| 1,573,608 A * | 2/1926 | Huffman | ........................... | 312/107 |
| 2,048,412 A * | 7/1936 | Sissman | ........................... | 249/130 |
| 2,255,153 A * | 9/1941 | Crowley | ........................... | 249/70 |
| 2,788,912 A * | 4/1957 | Simonsen | ........................... | 220/533 |
| 2,851,188 A * | 9/1958 | Pavelle | ........................... | 206/502 |
| 2,926,978 A * | 3/1960 | Mitchell | ........................... | 312/108 |
| 3,107,131 A * | 10/1963 | Lightburn | ........................... | 312/107 |
| 3,834,778 A * | 9/1974 | Morrison et al. | ........................... | 312/209 |
| 4,111,353 A * | 9/1978 | Collins et al. | ........................... | 229/120.16 |
| 4,436,215 A * | 3/1984 | Kleinert et al. | ........................... | 220/533 |
| 4,830,272 A * | 5/1989 | Wear et al. | ........................... | 229/120.15 |
| 5,036,989 A * | 8/1991 | Carilli | ........................... | 211/74 |
| 6,220,682 B1 * | 4/2001 | Vertullo | ........................... | 312/334.28 |
| 7,309,472 B2 * | 12/2007 | Michaelson et al. | ........................... | 422/297 |
| 8,099,967 B2 | 1/2012 | Jia | | |

OTHER PUBLICATIONS

VWR® Low and Ultra-Low Temperature Feezers, Brochure 1011 7M Lit. No. 92939, Jan. 2012 (8 pages).
Thermo Fisher Scientific Inc., "Thermo Scientific CryoExtra High-Efficiency Cryogenic Storage," Fisher Scientific Brochure No. BNO130126, CSCRYOEXTRA-CCG, Jan. 2012 (4 pages).

(Continued)

*Primary Examiner* — Darnell Jayne
*Assistant Examiner* — Timothy M Ayres
(74) *Attorney, Agent, or Firm* — Wood, Herron & Evans, LLP

(57) ABSTRACT

A sliding drawer storage rack for cold storage units includes a rack body and a plurality of shelves operatively coupled to the rack body. A drawer defines a storage cavity and is configured to be supported for sliding movement by at least one of the plurality of shelves. A plurality of divider lips extends upwardly from the drawer to divide the storage cavity into a plurality of box receptacles sized to receive a storage box. At least some of the plurality of shelves are defined by opposing first and second L-shaped supports laterally spaced from each other and coupled to the rack body, thereby reducing material use and weight of the storage rack.

18 Claims, 5 Drawing Sheets

(56) References Cited

OTHER PUBLICATIONS

Thermo Fisher Scientific Inc., "New! Thermo Scientific Forma Ultra-Low Temperature Freezers," Brochure BRCSFULT, Aug. 2011 (28 pages).
Thermo Fisher Scientific, Inc., "Thermo Scientific Revco Ultra-low Temperature Feezers" Brochure BRCSREVCOULT, Aug. 2011 (32 pages).
Fisher Scientific, "Isotemp®-86° Freezers," Fisher Scientific Brochure No. BN0630113, BRCSISOULT, Jul. 2011 (8 pages).
Thermo Fisher Scientific Inc., "New! Thermo Scientific TS Series Ultra-Low Temperature Freezers," BRCSTSULT, Aug. 2011 (28 pages).
Thermo Fisher Scientific Inc., "Thermo Scientific Cryopreservation Equipment," Brochure BRCSCRYO, Mar. 2010 (36 pages).
Thermo Fisher Scientific Inc., "New! Thermo Scientific HERAfreeze Ultra-Low Temperature Feezers," Brochure BRCSHERAULT, Aug. 2011 (28 pages).

* cited by examiner

SLIDING DRAWER STORAGE RACK FOR COLD STORAGE UNITS

FIELD OF THE INVENTION

The present invention relates generally to storage racks and, more particularly, to sliding drawer storage racks used with cold storage units such as upright freezers.

BACKGROUND OF THE INVENTION

Cold storage units such as freezers and dewars are used for various purposes, including the storage of biological samples over short and long periods of time. For example, biological materials for transplantation such as blood, tissue, or plasma may require storage for short periods of time before use. In another example, biological cells such as DNA samples may be stored for longer periods of time. Conventional cold storage units may be cooled by mechanical refrigeration circuits or by other methods, including the provision of liquid nitrogen ("LN2"). One type of cold storage unit used to store biological samples is known as an "ultra-low temperature freezer" ("ULT"), which is used to cool its inner storage chamber to relatively low temperatures such as about $-80°$ C. or lower, for example.

Known cold storage units are configured to contain a plurality of storage boxes supported on different types of storage racks within a cooled cabinet. One type of storage rack referred to as a sliding drawer storage rack is configured to contain a plurality of storage boxes and provide access to these storage boxes via sliding a drawer out from the storage rack. To this end, these sliding drawer storage racks include a rack body with first and second sidewalls and a plurality of shelves extending across the space between the first and second sidewalls. A plurality of drawers are slidably supported on each of the shelves, each drawer sized to hold a line or series of storage boxes lined up within a storage cavity defined by the drawer. The storage boxes are lined up along a central longitudinal axis of the drawer, which also defines a sliding movement direction of the drawer when a user moves a drawer to obtain access to the storage boxes stored therein. While material selection may vary, storage racks for cold storage units are often manufactured from either stainless steel or aluminum.

Although apertures are cut into each of the shelves and the rack body, the sliding drawer storage rack requires a significant amount of material to produce each of the shelves and drawers so as to extend across the entire width of the rack body. Furthermore, the frictional engagement of the drawers on the corresponding shelves can be difficult to overcome should the drawers freeze to one or more of the shelves during storage in the cryogenic temperatures of the cold storage unit. If the storage cavity of a particular drawer is not completely filled with storage boxes, the boxes that are stored in the drawer may slide along the length of the drawer during movement of the drawer. This uncontrolled sliding movement may make it more difficult to retrieve storage boxes that slide to the rear end of the storage rack and may also jostle the samples or materials held within the storage boxes.

There is a need, therefore, for a sliding drawer storage rack for use with a cold storage unit that reduces material weight necessary during assembly while providing improved performance compared to conventional storage racks.

SUMMARY OF THE INVENTION

In one embodiment, the invention provides a sliding drawer storage rack for holding a plurality of storage boxes within a cold storage unit. The storage rack generally includes a rack body, a plurality of shelves, a drawer, and a plurality of divider lips. The rack body includes a bottom wall and first and second opposed sidewalls extending upwardly from the bottom wall. The plurality of shelves is operatively coupled to the rack body and extends at least partially between the first and second sidewalls. Moreover, the drawer is configured to be supported for sliding movement on one of the plurality of shelves. The drawer includes a drawer bottom having a periphery and a drawer sidewall, the drawer sidewalls extending upwardly from the drawer bottom to define a storage cavity. The plurality of divider lips are configured to divide the storage cavity into a plurality of box receptacles sized to receive at least one of the storage boxes. The divider lips therefore prevent undesired sliding movement of storage boxes along the length of the drawer.

In one aspect, the drawer defines a central longitudinal axis oriented parallel to the first and second sidewalls of the rack body when the drawer is supported on one of the shelves. The drawer is slidable along the central longitudinal axis. Additionally, the plurality of divider lips is oriented generally transverse to the central longitudinal axis such that the storage boxes remain in position during sliding movement of the drawer. The plurality of divider lips may be provided on a divider insert positioned within the storage cavity. The divider insert includes a base plate configured to be supported by the drawer bottom and the plurality of divider lips, which are punched and bent upwardly from the base plate. Alternatively, the plurality of divider lips may be punched and bent upwardly from the drawer bottom.

In another aspect, the drawer further includes a plurality of projections formed from the same material as the drawer and extending downwardly from the drawer bottom such that the plurality of projections is configured to support the drawer on the shelf and thereby reduce frictional contact between the shelf and the drawer. For example, the each of the plurality of projections includes a dimple punched into the drawer bottom.

Also, at least one of the plurality of shelves is defined by a first L-shaped support operatively coupled to the first sidewall and a second L-shaped support operatively coupled to the second sidewall and opposing the first L-shaped support. The first and second L-shaped supports are laterally spaced from each other. Each of the first and second L-shaped supports includes a first leg coupled to the respective first or second sidewall and a second leg extending towards the second leg of the opposing L-shaped support. The use of the first and second L-shaped sidewalls reduces the material required to manufacture the sliding drawer storage rack because at least some of the shelves do not extend across the entire width of the storage rack, as each of the shelves did in conventional rack designs.

In yet another aspect, a bottom shelf of the plurality of shelves is defined by the bottom wall of the rack body extending between the first and second sidewalls. At least one of the shelves includes a rack reinforcement plate extending between the first and second sidewalls. Each of the shelves is spot welded to at least one of the first and second sidewalls, regardless of how the shelves are formed.

In another embodiment of the invention, a sliding drawer storage rack for holding storage boxes within a cold storage unit includes a rack body, a plurality of shelves, and a drawer. The rack body includes a bottom wall and first and second opposed sidewalls extending upwardly from the bottom wall. At least one of the shelves is defined by a first L-shaped support operatively coupled to the first sidewall and a second L-shaped support operatively coupled to the second sidewall and opposing the first L-shaped support. The first and second L-shaped supports are laterally spaced from one another. The drawer is configured to be supported for sliding movement on at least one of the plurality of shelves. The drawer holds storage boxes such that the storage boxes are accessible by sliding the appropriate drawer out of the rack body along the corresponding shelf. The use of the L-shaped supports reduces the amount of material needed to manufacture the storage rack.

According to another embodiment, the storage racks described above may be positioned within a cold storage unit. The cold storage unit includes a housing defining an interior volume, a door, and at least one of the sliding drawer storage racks. The interior volume is configured to be accessible via the door such that the sliding drawer storage racks are easily accessed.

These and other objects and advantages of the present invention will become more readily apparent during the following detailed description taken in conjunction with the drawings herein.

BRIEF DESCRIPTION OF THE DRAWINGS

The accompanying drawings, which are incorporated in and constitute a part of this specification, illustrate an embodiment of the invention and, together with a general description of the invention given above, and the detailed description given below, serve to explain the invention.

DETAILED DESCRIPTION

Figure 1:
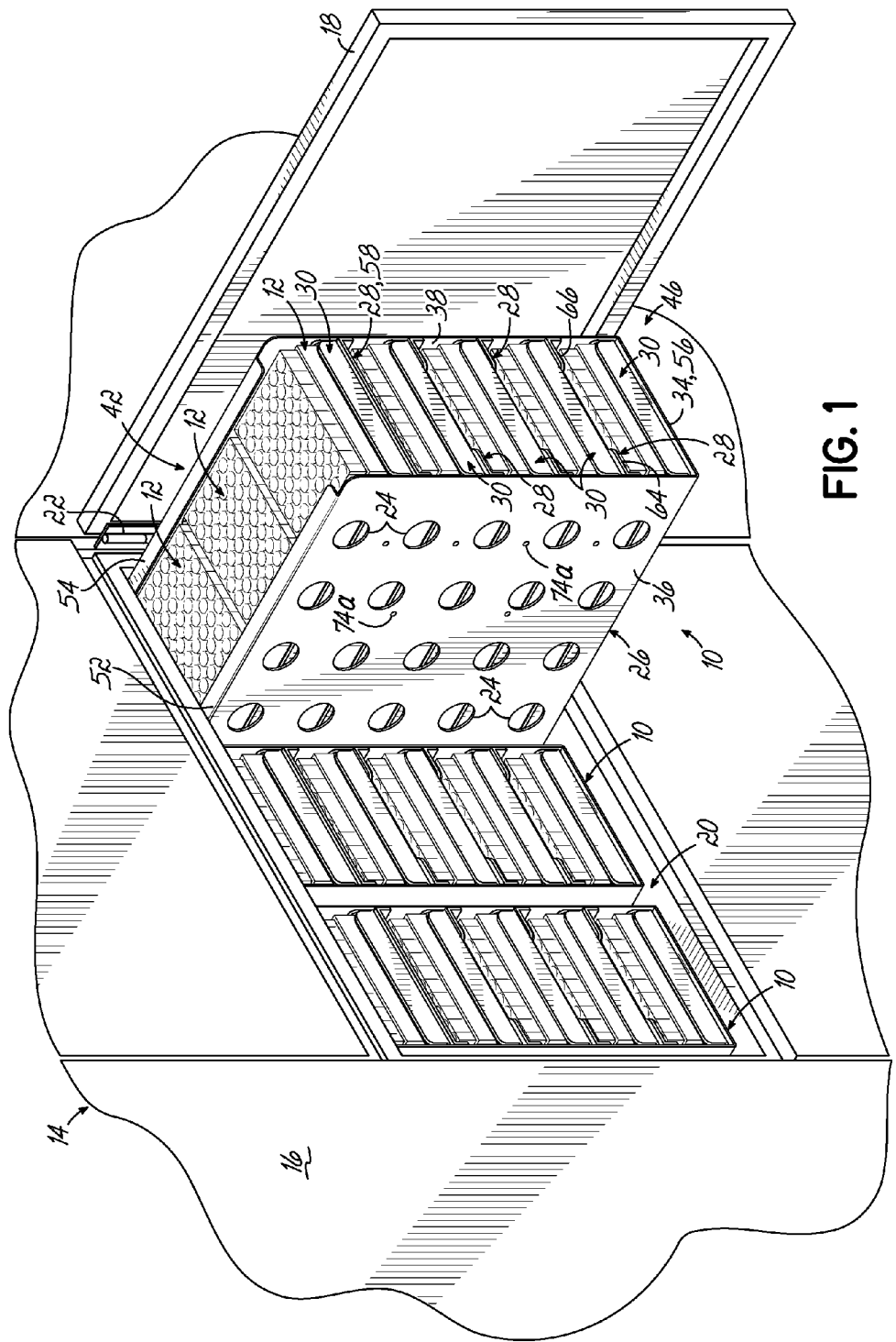
FIG. 1 is a perspective view of a cold storage unit including an exemplary embodiment of a sliding drawer storage rack according to the invention, with one storage rack moved partially out of a cabinet of the cold storage unit to illustrate storage boxes held by the storage rack.

With reference to FIG. 1, an exemplary embodiment of a sliding drawer storage rack 10 for holding storage boxes 12 (alternatively, "micro plates") is shown within a cold storage unit 14. More particularly, three storage racks 10 are shown in FIG. 1 with one partially pulled out of the cold storage unit 14 to better illustrate the storage boxes 12. Although the term "cold storage unit" is used throughout the specification, it will be understood that the sliding drawer storage rack 10 disclosed herein may be used with any type of cooling device, including refrigerators, freezers, and cryogenic vessels of any variety, collectively referred to hereinafter as "cold storage units." The storage boxes 12 typically contain a grid (not shown) or other internal structure for receiving and orienting a plurality of vials or tubes filled with biological samples in an array. However, the storage boxes 12 may be sized to receive other types of containers for biological samples. The cold storage unit 14 includes a housing 16 and a door 18 that may be arranged in any configuration to define an interior volume 20. The door 18 is pivotally coupled to the housing 16 and configured such that a user may open the door 18 to access the interior volume 20 of the cold storage unit 14 and close the door 18 to maintain the freezing conditions generally preferable for sample storage. More specifically, the door 18 is connected to the housing 16 by a hinge 22, thereby allowing the user to quickly access the storage boxes 12 within the interior volume 20 by pivoting the door 18 open and then moving drawers on the storage rack 10 to retrieve the appropriate storage box 12. It will be understood that the door 18 illustrated is an interior door that provides access to a particular portion of the interior volume 20 after a larger outer door (not shown) has been opened to provide access to a plurality of interior doors. Advantageously as described below, the sliding drawer storage rack 10 is designed with a reduced amount of material to reduce the weight and costs of manufacture, and the sliding drawer storage rack 10 also prevents unintentional sliding movement of storage boxes 12.

Throughout the following description, directional and orientation terms such as vertical, horizontal, top, bottom, front, and rear are used to describe the relative relation of elements of the sliding drawer storage rack 10, as used in the exemplary embodiment within a cold storage unit 14. However, it will be appreciated that these terms are used for illustrative purposes only and do not limit the storage rack 10 to formation and use in such orientations. For example, the sliding drawer storage rack 10 may be manufactured or stored within a cold storage unit in other orientations depending on the needs of the user.

The storage boxes 12 are held within the cold storage unit 14 by the storage rack 10. Depending on the size of the interior volume 20, any convenient number of storage racks 10 may be positioned within the interior volume 20. However, a maximum number of storage boxes 12 may be positioned within the cold storage unit 14 by densely packing the storage racks 10 side-by-side within the interior volume 20. In circumstances where the storage racks 10 and storage boxes 12 are densely packed, it is preferable to facilitate greater convection throughout the cold storage unit 14. Therefore, the storage rack 10 of this embodiment includes a plurality of first apertures 24 cut from solid surfaces (such as from a rack body 26) as described in further detail below. The first apertures 24 improve convection and also beneficially reduce the overall weight of the material needed to manufacture the storage rack 10. The plurality of first apertures 24 may be punched from the storage rack 10 or cut by other known methods. As shown within FIG. 1, the storage racks 10 are configured to be easily removable from the interior volume 20 to facilitate simple installation, cleaning, and other routine maintenance, as may be required.

Figure 2:
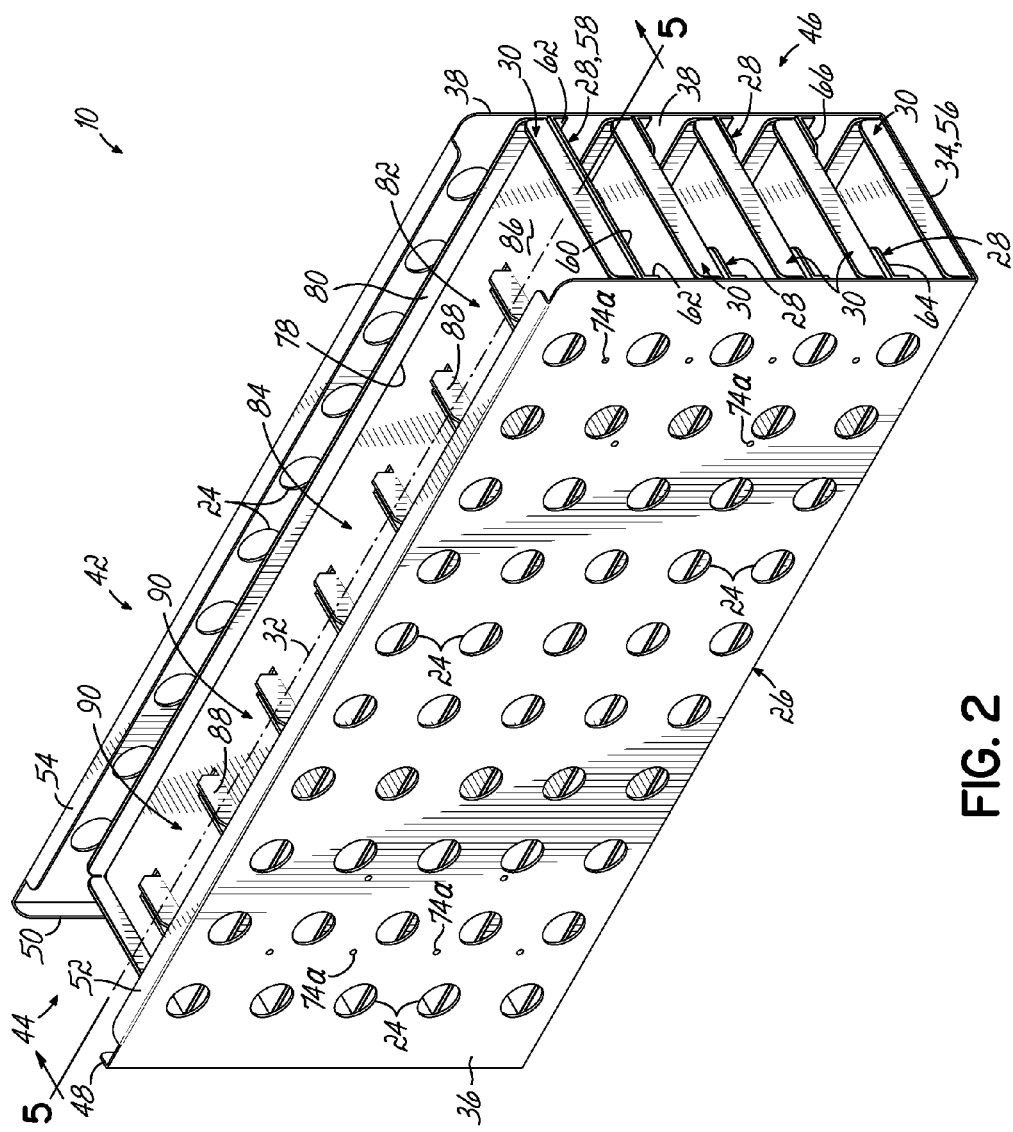
FIG. 2 is a perspective view of the storage rack of FIG. 1 with the storage boxes removed.
Figure 3:
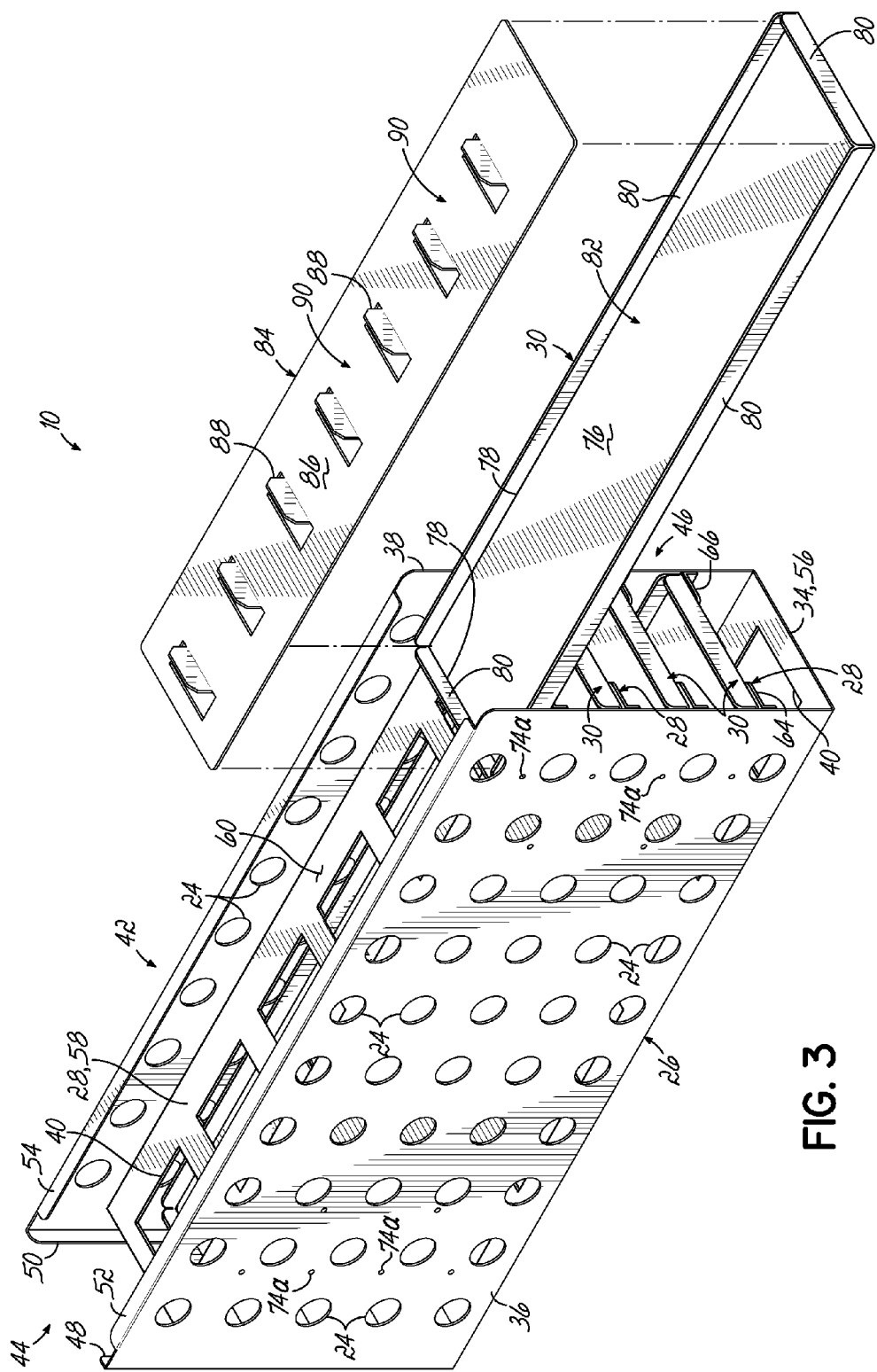
FIG. 3 is a partially exploded view of the storage rack of FIG. 2, showing additional details of a shelf, a drawer, and a divider insert used with the storage rack.

The exemplary embodiment of the slider drawer storage rack 10 is shown in further detail in FIGS. 2 through 5. FIGS. 2 and 3 show perspective views of the storage rack 10 without storage boxes 12 such that the elements comprising the storage rack 10 are readily visible. The storage rack 10 includes a rack body 26 and a plurality of shelves 28 operatively coupled to the rack body 26. A drawer 30 is positioned on each of the shelves 28 and supported by each shelf 28 for sliding movement relative to the rack body 26. In other words, a user may slide the drawer 30 along a central longitudinal axis 32 to access storage boxes 12 held by the drawer 30. Preferably, the drawer 30 slides along the central longitudinal axis 32 while the rack body 26 remains within the interior volume 20 of the cold storage unit 14 to provide selective access and visibility of the storage boxes 12 without requiring the movement of the entire storage rack 10 out of the interior volume 20. While the rack body 26, the plurality of shelves 28, and the drawers 30 may be manufactured from any suitable material, the rack body 26 and the plurality of shelves 28 are preferably manufactured from stainless steel 201, while the drawers 30 are preferably manufactured from aluminum.

As shown in FIG. 3, the rack body 26 includes a bottom wall 34 and first and second opposed sidewalls 36, 38 extending upwardly from the bottom wall 34 to form a generally U-shaped rack body 26. The first and second sidewalls 36, 38 are generally vertically oriented, parallel to each other, and offset such that the drawers 30 will extend at least partially between the first and second sidewalls 36, 38. The plurality of first apertures 24 described above are cut into the first and second sidewalls 36, 38 and are generally round in shape and patterned in rows and columns along the entirety of the first and second sidewalls 36, 38. Additionally, a plurality of square-shaped, second apertures 40 are cut into the bottom wall 34. The size and number of the pluralities of first and second apertures 24, 40 are configured to provide both minimized use of material and desirable levels of convection throughout the entire storage rack 10 while also maintaining sufficient structural integrity. It will be understood that the size, shape, and number of the first and second apertures 24, 40 may be modified without departing from the scope of the invention.

In addition, the rack body 26 defines a top side 42 defined by the free ends of the sidewalls 36, 38, a rear end 44, and a front end 46. The drawers 30 are configured to be accessed and moved through the front end 46. The top side and rear end 42, 44 are each configured to block storage boxes 12 and/or drawers 30 from moving through the top side 42 or rear end 44. In contrast, the front end 46 is open so that the plurality of drawers 30 may slide forward when being removed by the user. More specifically, the top side 42 and rear end 44 include inwardly bent vertical and horizontal lips 48, 50, 52, 54 extending from the first and second sidewalls 36, 38. The vertical lips 48, 50 are vertically oriented at the rear end 44 and include a first vertical lip 48 bent from the first sidewall 36 a second vertical lip 50 bent from the second sidewall 38. Similarly, the horizontal lips 52, 54 are horizontally oriented at the top side 42 and include a first horizontal lip 52 bent from the first sidewall 36 a second horizontal lip 54 bent from the second sidewall 38. Furthermore, the plurality of vertical and horizontal lips 48, 50, 52, 54 also provide additional stiffness and rigidity to the rack body 26.

Figure 4:
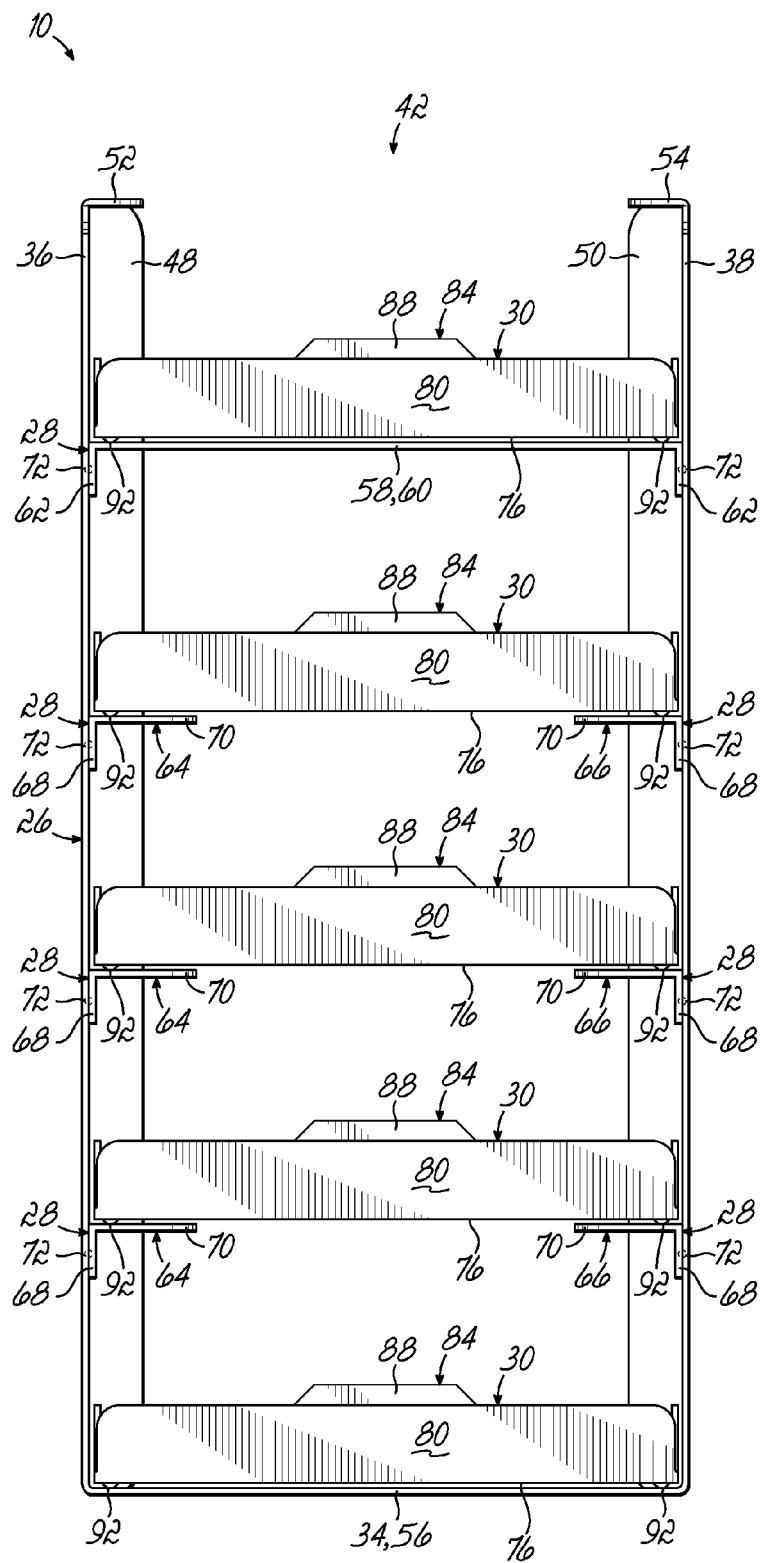
FIG. 4 is a front elevational view of the storage rack of FIG. 2.
Figure 5:
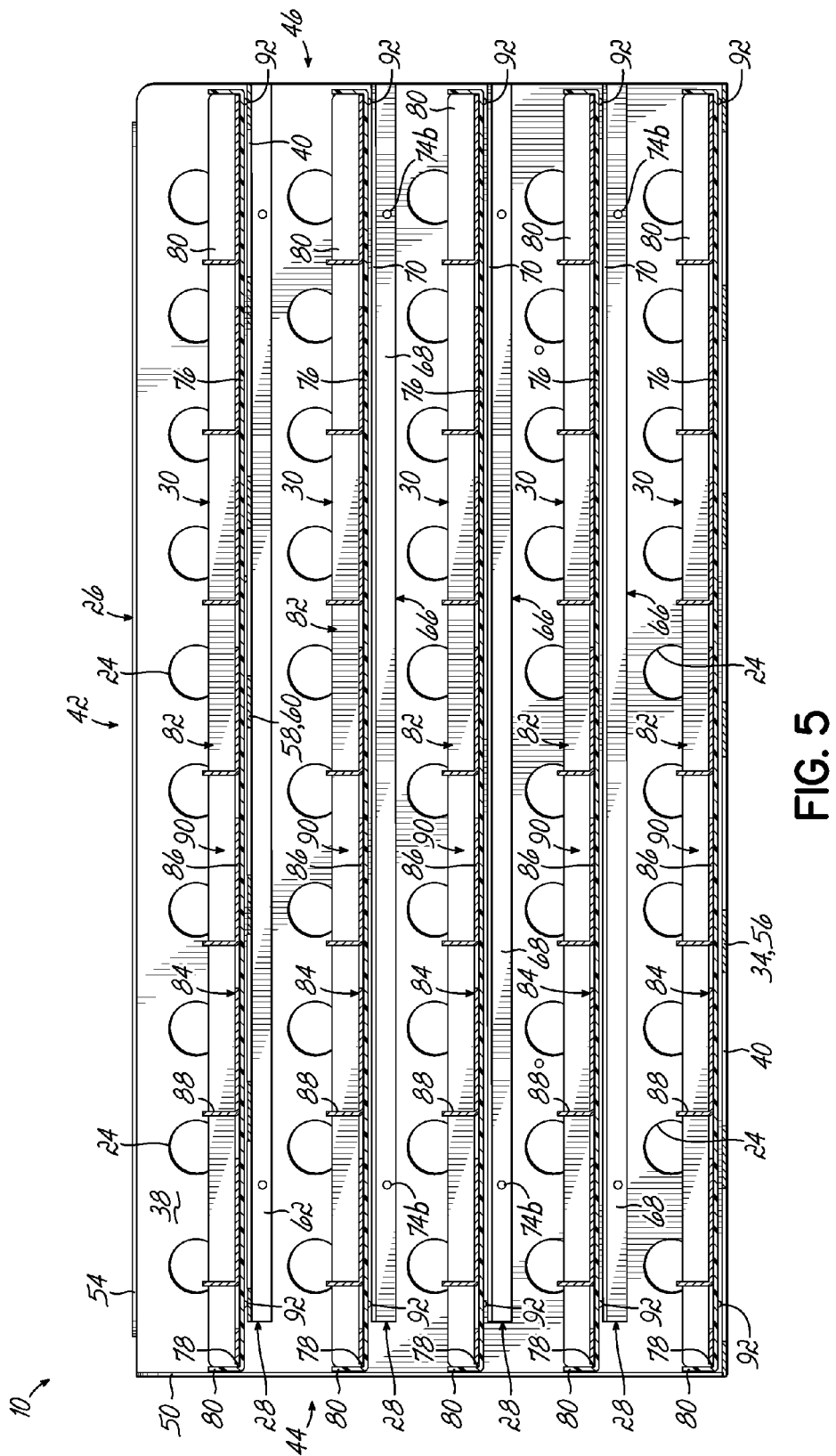
FIG. 5 is a cross sectional side view of the storage rack of FIG. 2, taken along line 5-5, to illustrate additional features of the shelves, drawers, and divider inserts used with the storage rack.

As shown in FIGS. 3 through 5, the plurality of shelves 28 includes a bottom shelf 56 defined by the bottom wall 34 and a top shelf 58 being located farthest from the bottom wall 34 relative to each of the other shelves 28. The top shelf 58 includes a rack reinforcement plate 60 extending across the entire width between the first and second sidewalls 36, 38. Similar to the bottom wall 34, the rack reinforcement plate 60 also includes a plurality of second apertures 40 to reduce weight. The rack reinforcement plate 60 provides additional structural rigidity of the storage rack 10 adjacent to the top side 42. Moreover, the rack reinforcement plate 60 includes end tabs 62 bent downwardly to reside adjacent to and in abutting relation with the first and second sidewalls 36, 38. The rack reinforcement plate 60 is coupled to the rack body 26 by spot welding these end tabs 62 to the sidewalls 36, 38.

The plurality of shelves 28 also includes at least some shelves defined by first and second L-shaped supports 64, 66 opposing one another. As best shown in FIG. 4, each pair of the first and second L-shaped supports 64, 66 is spaced apart from each other and coupled to the first and second sidewalls 36, 38. More particularly, each first and second L-shaped support 64, 66 includes a first leg 68 and a second leg 70. The first leg 68 extends in abutting relation with the corresponding first or second sidewall 36, 38 and is coupled to the corresponding first or second sidewall 36, 38 by spot welding, while the second leg 70 extends inward toward the second leg 70 of the opposing L-shaped support 64, 66. As such, the first and second L-shaped supports 64, 66 collectively define at least some of the plurality of shelves 28 located between the bottom shelf 56 and the top shelf 58. Preferably, each of the remaining shelves 28 other than the bottom and top shelves 56, 58 is defined by the corresponding pairs of first and second L-shaped supports 64, 66. The L-shaped supports 64, 66 and the end tabs 62 of the rack reinforcement plate 60 are coupled to the first and second sidewalls 36, 38 via a plurality of spot welds 72. Although the spot welds 72 between the first and second sidewalls 36, 38 and the shelves 28, 58 are shown schematically in FIG. 4, it will be appreciated that other methods of coupling the shelves 28, 58 to the rack body 26 may be used in other embodiments. Regardless of the method of coupling used, assembly of the storage rack 10 is simplified by the provision of a plurality of alignment apertures 74a, 74b shown in FIGS. 1 through 3 and 5. More specifically, the rack body 26 may include one or more first alignment apertures 74a (see FIGS. 1 through 3) that are configured to be adjacent to one or more second alignment apertures 74b (see FIG. 5) positioned on each of the shelves 28, 58 when the shelves 28, 58 are coupled to the rack body 26. In this regard, an operator simply aligns the first and second alignment apertures 74a, 74b and spot welds the elements together at that location. As such, aligning and coupling the shelves 28, 58 with the rack body 26 during manufacturing may be performed with greater speed and accuracy.

With continued reference to FIGS. 3 through 5, the drawer 30 further includes a drawer bottom 76 having a periphery 78. At the periphery 78, a drawer sidewall 80 extends upward from the drawer bottom 76 to define a storage cavity 82 configured to receive storage boxes 12. In the exemplary embodiment of the invention, a divider insert 84 is also positioned within the storage cavity 82. The divider insert 84 includes a base plate 86 and a plurality of divider lips 88. Preferably, the base plate 86 and the plurality of divider lips 88 are formed from a single piece of material, such as aluminum, the plurality of divider lips 88 being punched from the base plate 86. Once the plurality of divider lips 88 are punched out, each of the divider lips 88 is bent upward and generally perpendicular relative to the base plate 86. Each one of the plurality of divider lips 88 is oriented generally transverse to the central longitudinal axis 32 of the drawer 30 when the divider insert 84 is located in the storage cavity 82. According to the exemplary embodiment, the divider insert 84 is laid within the storage cavity 82 to reside in abutting relation with the drawer bottom 76. By positioning each of the plurality of divider lips 88 in this transverse orientation, the storage cavity 82 is thereby divided into a plurality of box receptacles 90. Each of the box receptacles 90 is sized to receive one or more storage boxes 12. Preferably, each of the plurality of box receptacles 90 is configured to receive only one storage box 12. In this regard, the divider lips 88 prevent undesirable sliding movement of storage boxes 12 along the length of the drawer 30. In alternative embodiments, it may be possible to position the divider lips 88 in other orientations for dividing the storage cavity 82 into box receptacles 90 of varying shape and size. It will be understood that the plurality of divider lips 88 may be spot welded to the drawer 30 or formed in a unitary manner with the drawer 30 (specifically as a punched-up part of the drawer bottom 76) in other embodiments consistent with the scope of the invention.

Furthermore, and as most clearly illustrated in FIGS. 4 and 5, the drawer 30 also includes a plurality of projections 92 extending downwardly from the drawer bottom 76. In the exemplary embodiment, each of the projections 92 is a dimple punched into the drawer bottom 76 so as to extend downwardly from the drawer bottom 76. Therefore, the plurality of projections 92 are formed from the same material as the drawer 30. The plurality of dimples 92 is configured to support the drawer 30 on any one of the plurality of shelves 28. The dimples 92 reduce frictional contact between the shelf 28 and the drawer 30 because the surface area contact between the drawer 30 and the shelf 28 is reduced to only the dimples 92. As a result, frost or similar frozen conditions will not tend to cause the drawer 30 to become immovably frozen to any one of the plurality of shelves 28 along a large contacting surface area. In the exemplary embodiment, the drawer 30 includes four dimples 92 distributed evenly on the drawer bottom 76 to minimize frictional contact with the corresponding shelf 28. It will be understood that the number, distribution, and shape of the dimples 92 on the drawer 30 may be modified in other embodiments without departing from the scope of the invention.

While the present invention has been illustrated by the description of an exemplary embodiment thereof, and while this embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A storage rack for holding a plurality of storage boxes within a cold storage unit, comprising:
   a rack body including a bottom wall and first and second opposed sidewalls extending upwardly from the bottom wall;
   a plurality of shelves operatively coupled to the rack body and extending at least partially between the first and second sidewalls;
   a drawer configured to be supported for sliding movement on one of the plurality of shelves, the drawer including a drawer bottom having a periphery and a drawer sidewall, the drawer sidewall extending upwardly from the drawer bottom to define a storage cavity; and
   a plurality of divider lips extending upwardly from the drawer bottom and spaced from the drawer sidewall, the divider lips cooperating with the drawer sidewall to divide the storage cavity into a single row of box receptacles sized to receive at least one of the storage boxes, with each of the box receptacles in the storage cavity being delimited in a first direction by the drawer sidewall and being delimited in another direction transverse to the first direction by at least one of the divider lips.

2. The storage rack of claim 1, wherein the drawer defines a central longitudinal axis oriented parallel to the first and second sidewalls of the rack body when the drawer is supported on one of the shelves, the drawer being slideable along the central longitudinal axis, and wherein the plurality of divider lips are oriented generally transverse to the central longitudinal axis such that the storage boxes remain in position during sliding movement of the drawer.

3. The storage rack of claim 1, further comprising:
   a divider insert positioned within the storage cavity of the drawer, the divider insert including a base plate configured to be supported by the drawer bottom and the plurality of divider lips, which are punched and bent upwardly from the base plate.

4. The storage rack of claim 1, wherein the box receptacles are at least partially defined by a bottom surface, and the plurality of divider lips are punched and bent upwardly from the bottom surface such that the bottom surface and the divider lips are defined by a single unitary piece of material.

5. The storage rack of claim 1, wherein the drawer further includes a plurality of projections formed from the same material as the drawer and extending downwardly from the drawer bottom, the plurality of projections being configured to support the drawer on the shelf.

6. The storage rack of claim 5, wherein each of the projections comprises a dimple punched into the drawer bottom.

7. The storage rack of claim 1, wherein the rack body includes a front end and a rear end, and wherein at least one of the shelves is defined by a first L-shaped support coupled to the first sidewall and a second L-shaped support coupled to the second sidewall and opposing the first L-shaped support, wherein each of the first and second L-shaped supports includes a first leg coupled to the respective first or second sidewall and a second leg extending towards the second leg of the opposing L-shaped support, the second legs of the first and second L-shaped supports each defining an elongate terminal edge extending between the front and rear ends of the rack body and facing towards the second leg of the opposing L-shaped support, the first and second L-shaped supports being laterally spaced from each other such that a gap is defined between the elongate terminal edges of the second legs without connections formed between the second legs across the gap.

8. The storage rack of claim 1, wherein at least one of the plurality of shelves comprises a rack reinforcement plate extending between the first and second sidewalls.

9. The storage rack of claim 7, wherein the drawer further includes a drawer bottom and a plurality of projections formed from the same material as the drawer and extending downwardly from the drawer bottom, the plurality of projections being configured to support the drawer on the shelf.

10. The storage rack of claim 9, wherein each of the projections comprises a dimple punched into the drawer bottom.

11. The storage rack of claim 7, wherein at least one of the plurality of shelves comprises a rack reinforcement plate extending between the first and second sidewalls.

12. The storage rack of claim 7, further comprising:
    a divider insert configured to separate a storage cavity within the drawer into the single row of box receptacles sized to receive the storage boxes.

13. The storage rack of claim 1, further comprising:
    a plurality of storage boxes removably inserted into the box receptacles.

14. A cold storage unit for storing a plurality of storage boxes, comprising;
    a housing defining an interior volume;
    a door adjacent to the housing, the door being configured to open to provide access to the interior volume; and
    a storage rack positioned within the interior volume, the storage rack including:
       a rack body including a bottom wall and first and second opposed sidewalls extending upwardly from the bottom wall;
       a plurality of shelves operatively coupled to the rack body and extending at least partially between the first and second sidewalls;
       a drawer configured to be supported for sliding movement on one of the plurality of shelves, the drawer including a drawer bottom having a periphery and a drawer sidewall, the drawer sidewall extending upwardly from the drawer bottom to define a storage cavity; and a plurality of divider lips extending upwardly from the drawer bottom and spaced from the drawer sidewall, the divider lips cooperating with the drawer sidewall to divide the storage cavity into a single row of box receptacles sized to receive at least one of the storage boxes, with each of the box receptacles in the storage cavity being delimited in a first direction by the drawer sidewall and being delimited in another direction transverse to the first direction by at least one of the divider lips.

15. The cold storage unit of claim 14, wherein the drawer defines a central longitudinal axis oriented parallel to the first and second sidewalls of the rack body when the drawer is supported on one of the shelves, the drawer being slideable along the central longitudinal axis, and wherein the plurality of divider lips are oriented generally transverse to the central longitudinal axis such that the storage boxes remain in position during sliding movement of the drawer.

16. The cold storage unit of claim 14, wherein the storage rack further includes:

a divider insert positioned within the storage cavity of the drawer, the divider insert including a base plate configured to be supported by the drawer bottom and the plurality of divider lips, which are punched and bent upwardly from the base plate.

17. The cold storage unit of claim 14, wherein the box receptacles are at least partially defined by a bottom surface, and the plurality of divider lips are punched and bent upwardly from the bottom surface such that the bottom surface and the divider lips are defined by a single unitary piece of material.

18. The cold storage unit of claim 14, wherein the rack body extends between a front end and a rear end; and wherein at least one of the shelves is defined by a first L-shaped support operatively coupled to the first sidewall and a second L-shaped support operatively coupled to the second sidewall and opposing the first L-shaped support, wherein each of the first and second L-shaped supports includes a first leg coupled to the respective first or second sidewall and a second leg extending towards the second leg of the opposing L-shaped support, the second legs of the first and second L-shaped supports each defining an elongate terminal edge extending between the front and rear ends of the rack body and facing towards the second leg of the opposing L-shaped support, the first and second L-shaped supports being laterally spaced from each other such that a gap is defined between the elongate terminal edges of the second legs without connections formed between the second legs across the gap.

\* \* \* \* \*

UNITED STATES PATENT AND TRADEMARK OFFICE
CERTIFICATE OF CORRECTION

| | | |
|---|---|---|
| PATENT NO. | : 8,851,588 B2 | Page 1 of 1 |
| APPLICATION NO. | : 13/488622 | |
| DATED | : October 7, 2014 | |
| INVENTOR(S) | : Dennis D. Ward et al. | |

It is certified that error appears in the above-identified patent and that said Letters Patent is hereby corrected as shown below:

In the Specification,

Column 2, line 36, delete "shelf and the drawer. For example, the each of the plurality of" and add -- shelf and the drawer. For example, each of the plurality of --

Column 7, line 28, delete "departures may be from such details without departing from" and add -- departures may be made from such details without departing from --

In the Claims,

Claim 14, Column 8, line 53, delete "boxes, comprising;" and add -- boxes, comprising: --

Signed and Sealed this
Tenth Day of March, 2015

Michelle K. Lee
*Deputy Director of the United States Patent and Trademark Office*